United States Patent
Rowe

(10) Patent No.: US 11,513,110 B2
(45) Date of Patent: Nov. 29, 2022

(54) DRILL BIT WEAR

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 572 days.

(21) Appl. No.: 16/583,884

(22) Filed: Sep. 26, 2019

(65) Prior Publication Data

US 2021/0095528 A1 Apr. 1, 2021

(51) Int. Cl.
*G01N 33/28* (2006.01)
*E21B 12/02* (2006.01)
*G01N 1/22* (2006.01)
*G01N 33/00* (2006.01)
*E21B 49/08* (2006.01)
*C10G 9/00* (2006.01)

(52) U.S. Cl.
CPC ......... *G01N 33/2823* (2013.01); *E21B 12/02* (2013.01); *E21B 49/0875* (2020.05); *G01N 1/2202* (2013.01); *G01N 33/005* (2013.01); *G01N 33/2835* (2013.01); *C10G 9/00* (2013.01)

(58) Field of Classification Search
CPC ............... G01N 1/2202; G01N 33/005; G01N 33/2823; G01N 33/2835; E21B 12/02; E21B 49/003; E21B 49/08; E21B 49/0875; C10G 9/00
See application file for complete search history.

(56) References Cited

U.S. PATENT DOCUMENTS

| | | |
|---|---|---|
| 10,167,676 B2 | 1/2019 | Calleri |
| 2010/0025110 A1 | 2/2010 | John et al. |
| 2015/0240627 A1 | 8/2015 | Gao et al. |
| 2017/0234127 A1 | 8/2017 | Bartetzko et al. |

FOREIGN PATENT DOCUMENTS

CA 2223662 A1 6/1999

OTHER PUBLICATIONS

PCT Application Serial No. PCT/US2019/053321, International Search Report, dated Jun. 24, 2020, 3 pages.
PCT Application Serial No. PCT/US2019/053321, International Written Opinion, dated Jun. 24, 2020, 4 pages.

(Continued)

*Primary Examiner* — Benjamin R Schmitt
(74) *Attorney, Agent, or Firm* — Delizio, Peacock, Lewin & Guerra

(57) ABSTRACT

Drill bit wear can be quantified through an analysis of chemical reactions that occur during drilling. A detector measures the molar composition of a dissolved gas sample. From the molar composition, the moles of hydrogen, ethylene, and propylene in the dissolved gas sample are determined. A thermal cracking reaction and a thermal decomposition reaction determine moles of hydrogen produced during drill bit wear based on the moles of ethylene and propylene. The moles of hydrogen produced is subtracted from the total moles of hydrogen to determine moles of hydrogen produced by metal oxidation. A metal-water reaction determines the moles of metal that have been oxidized. This can be converted into mass or volume of metal loss to quantify drill bit wear.

14 Claims, 4 Drawing Sheets

(56) References Cited

OTHER PUBLICATIONS

"$15M USD Saved Through Bit Trip Optimization", GeoLog Surface Logging, Case Study: BitLife, 2019, 1 page, retrieved on May 20, 2019 from https://www.geolog.com/files/pdf/bitlife_case.pdf.

Sattler, et al., "Catalytic Dehydrogenation of Light Alkanes on Metals and Metal Oxides", American Chemical Society, Chemical Reviews, vol. 114, No. 20, Aug. 27, 2014, pp. 10613-10653.

Sedighi, et al., "Experimental Study And Optimization Of Heavy Liquid Hydrocarbon Thermal Cracking To Light Olefins By Response Surface Methodology", Korean Journal of Chemical Engineering, vol. 27, Issue 4, Jul. 2010, pp. 1170-1176.

Sie, "Acid-Catalyzed Cracking of Paraffinic Hydrocarbons. 1. Discussion of Existing Mechanisms and Proposal of a New Mechanism", American Chemical Society, Industrial & Engineering Chemistry Research, vol. 31, No. 8, Aug. 1, 1992, pp. 1881-1889.

Sundaram, et al., "Modeling Of Thermal Cracking Kinetics. 3. Radical Mechanisms For The Pyrolysis Of Simple Paraffins, Olefins, And Their Mixtures", American Chemical Society, Industrial & Engineering Chemistry Fundamentals, vol. 17, No. 3, Aug. 1, 1978, pp. 174-182.

Wenger, et al., "Drill Bit Metamorphism: Recognition and Impact on Show Evaluation", Society of Petroleum Engineers, Document ID SPE-125218-MS, Annual Technical Conference and Exhibition, Oct. 4-7, New Orleans, Louisiana, 2009, 9 pages.

Wu, et al., "Comparison of Liquid-Phase and Gas-Phase Pure Thermal Cracking of n-Hexadecane", American Chemical Society, Industrial & Engineering Chemistry Research, vol. 35, No. 12, Dec. 4, 1996, pp. 4747-4754.

Xie, et al., "Thermal Cracking of Oil under Water Pressure up to 900 bar at High Thermal Maturities. 1. Gas Compositions and Carbon Isotopes", American Chemical Society, Energy & Fuels, vol. 30, No. 4, Mar. 4, 2016, pp. 2617-2627, retrieved on May 20, 2019 from http://nora.nerc.ac.uk/id/eprint/513493/1/Xie%20et%20al%20Energy%20and%20Fuels%202016.pdf.

Yavor, et al., "Comparative Reactivity Of Industrial Metal Powders With Water For Hydrogen Production", Hydrogen Energy Publications, LLC, Published by Elsevier Ltd., 2014, pp. 1026-1036.

Yu, et al., "Thermal Decomposition of C10—C14 Normal Alkanes in Near-Critical and Supercritical Regions: Product Distributions and Reaction Mechanisms", American Chemical Society, Industrial & Engineering Chemistry Research, vol. 36, No. 3, Mar. 3, 1997, pp. 574-584.

DRILL BIT WEAR

BACKGROUND

The disclosure generally relates to the field of chemistry, and more particularly to cracking hydrocarbon oils.

Thermal cracking is the process of splitting large, heavy hydrocarbon molecules (alkanes) into smaller, lighter components (alkenes). Under high temperatures, the carbon-carbon bonds in alkanes break down to produce alkenes, such as ethylene and propylene. The rate of cracking and the end products are temperature dependent. During drilling operations, high drill bit speeds generate additional heat at the drill bit-rock formation interface that leads to thermal cracking of oil-based drilling fluid. The alkenes that are produced during the thermal cracking process do not naturally occur in hydrocarbon reservoirs. As such, the presence of alkenes in the drilling fluid can indicate wear on the drill bit due to contact with the rock formation.

BRIEF DESCRIPTION OF THE DRAWINGS

Embodiments of the disclosure may be better understood by referencing the accompanying drawings.

DESCRIPTION

Figure 1:
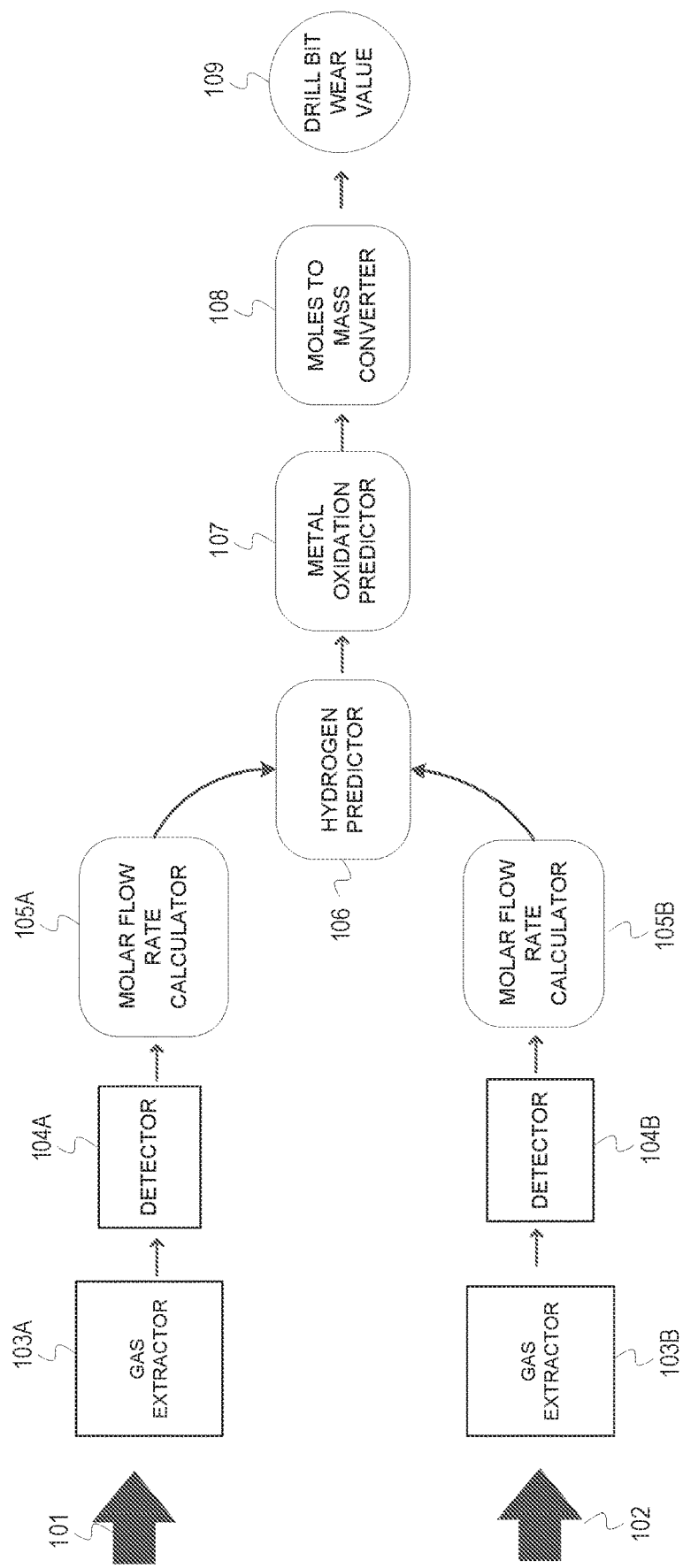
FIG. 1 depicts a schematic diagram of the process of quantifying drill bit wear.

The description that follows includes example systems, methods, techniques, and program flows that embody embodiments of the disclosure. However, it is understood that this disclosure may be practiced without these specific details. For instance, this disclosure refers to identifying when drill bit wear is occurring in illustrative examples. Aspects of this disclosure can also be applied to identify when a drill bit is not cutting efficiently. In other instances, well-known instruction instances, protocols, structures and techniques have not been shown in detail in order not to obfuscate the description.

Overview

During drilling activity, abrasive wear on a drill bit occurs due to contact with a rock formation. Over time, drill bit wear leads to the need to replace the drill bit. This causes non-productive time due to not being able to drill. Optimizing drilling operations to reduce drill bit wear allows for longer periods of drilling before the drill bit needs to be replaced. Even under optimized drilling conditions, the drill bit will eventually need to be removed. Quantifying drill bit wear while drilling maximizes effective drilling time and reduces non-productive time. Pulling the drill bit out too early can result in a loss of valuable drilling time if the drill bit still has more wear life remaining. However, removing the drill bit too late can result in non-productive time due to inefficient drilling and possibly compromise wellbore design. By quantifying drill bit wear while drilling, a drill bit removal strategy can be planned based on the drill bit wear.

Drill bit wear can be quantified based on two gas production modes. The first mode is hydrocarbon cracking, or thermal cracking. Thermal cracking is a precursor component of drill bit wear. Thermal cracking correlates to approaching drill bit wear, indicating that inefficient drilling is occurring which can lead to drill bit wear. Thermal cracking indicators include the presence of alkenes, such as ethylene and propylene. The second mode of gas production, thermal decomposition, occurs once drill bit degradation begins. Thermal decomposition indicators include the presence of hydrogen and carbon dioxide due to the oxidation of the drill bit. Drill bit mass is lost during thermal decomposition. Both modes can occur simultaneously with similar chemical signatures. Detecting the presence of these indicators and distinguishing between the two modes by separating the chemical signatures provides a technique for optimizing drilling and drill bit removal strategies. Thus, a technique is presented to quantify the total mass or volume loss of the drill bit due to drill bit wear through an analysis of the chemicals present in a drilling fluid.

Quantifying drill bit wear based on the aforementioned gas production modes involves determining molar composition of drilling fluid flow in ("flow in") and drilling fluid flow out ("flow out"). The molar composition gives the molar chemical complexion of the drilling fluid. The molar composition accounts for all components present in the drilling fluid in terms of mole fractions for each element. From the molar composition, the moles of select drilling fluid chemical species, such as hydrogen, ethylene, and propylene, are determined. With the molar compositions of the flow in and the flow out, the molarity, or molar concentration per unit volume of the fluid, of the select drilling fluid chemical species is calculated for each of flow in and flow out based on the fluid flow rate through an extractor. The molarity of each species for the flow in is subtracted from the respective molarity of each species for the flow out to determine the total moles of each chemical species produced. The moles of ethylene and propylene are summed and used to predict hydrogen production during non-optimized drilling based on a thermal cracking reaction. A thermal decomposition reaction is used to determine hydrogen produced during drill bit wear. The hydrogen produced during thermal cracking and thermal decomposition is subtracted from the total hydrogen to determine the hydrogen produced due to metal oxidation. By knowing the hydrogen produced during metal oxidation and the gross metal composition and average and/or oxidation state of the drill bit, the moles of metal that have been oxidized are back-calculated through stoichiometry of a metal-water reaction. The molecular weight and density can be used to convert moles to mass and volume, respectively.

Separating the chemical signatures of the two modes of gas production to quantify drill bit wear while drilling identifies when the drill bit is wearing. This can be used as an indication to adjust a drilling parameter or remove the drill bit from the wellbore. It also indicates that drilling parameters may not be optimized and are collectively causing thermal cracking to occur. Adjusting the drilling parameters to optimize drilling based on this indication leads to longer productive drilling times and reduced bit wear. This drill bit wear quantification can also be used to identify when a drill bit is not cutting efficiently, which can indicate hidden non-production time.

Example Illustrations

FIG. 1 depicts a schematic diagram of the process of quantifying drill bit wear. The process for determining drill bit wear involves monitoring the properties of fluid flow into and out of extractors. The chemical properties of the fluids are analyzed to quantify drill bit wear through a series of calculations based on chemical reactions. FIG. 1 depicts a visual summary of the process of determining drill bit wear.

Extractors 103A and 103B are connected to fluid flow in 101 and fluid flow out 102. Extractors 103A and 103B remove dissolved gas from the fluids. The dissolved gas flows from the extractors 103A and 103B into detectors 104A and 104B. The detectors 104A and 104B determine the molar composition of the dissolved gas samples. The detectors 104A, 104B determine all components present in the dissolved gases. This includes chemical species, such as hydrogen, ethylene, and propylene, as well as other gases, such as carbon dioxide or oxygen. Once the molar composition of the dissolved gas samples is determined, molar flow rate calculators 105A and 105B calculate the molar flow rates for each dissolved gas sample. The molar flow rate calculators 105A and 105B use the molar composition of the dissolved gas samples and the Law of Conservation of Mass to determine moles of hydrogen, ethylene, and propylene present in the dissolved gas samples. The calculated moles for each species are divided by the fluid flow rate through the extractors 103A and 103B to determine molarity.

A hydrogen predictor 106 subtracts the molarity of each species for the fluid flow in from the respective molarity of each species for the fluid flow out. A correction (delta) for time to flow through the wellbore is applied to the molarity of each species. The correction delta adjusts the molarities by accounting for any lag in time between the fluid flow from the detector through the wellbore to the drill bit and fluid flow from the drill bit back to the detector. This allows for calculations to effectively occur at the drill bit. The delta for each species is multiplied by the volumetric flow rate through the wellbore to give the total number of moles for each species being produced. The moles of ethylene and propylene are summed and used to calculate the moles of hydrogen produced. The moles of hydrogen produced is subtracted from the total moles of hydrogen. A metal oxidation predictor 107 back-calculates the moles of metal that have been oxidized using stoichiometry based on the moles of hydrogen produced. Gross metal composition of the drill bit and possible and/or average oxidation state of the metal comprising the drill bit is incorporated into the metal oxidation prediction. A mole to mass converter 108 determines the mass of metal oxidized by using the molecular weight and the calculated moles of metal oxidized. The mass can be converted to volume using the density of the metal. Once the mass of metal oxidized is determined, a drill bit wear value 109 is produced that quantifies drill bit wear. The drill bit wear 109 is the mass of metal removed from the drill bit during the drilling process.

Figure 2:
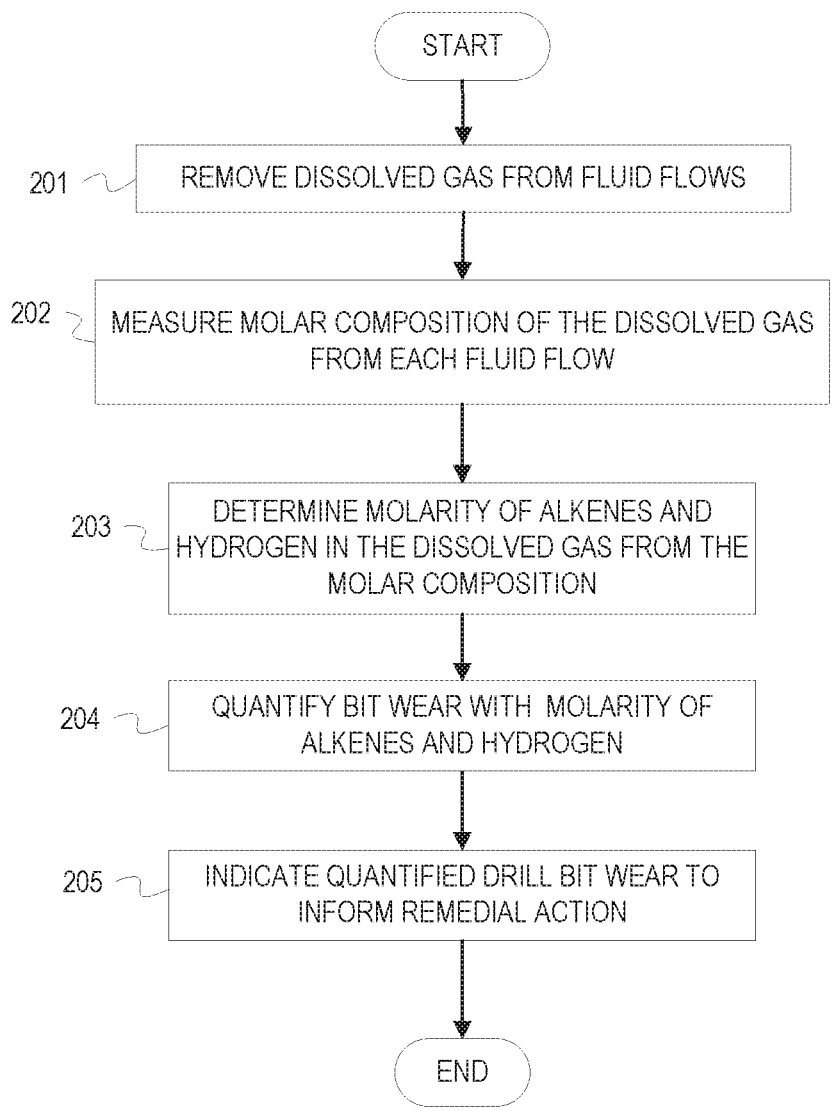
FIG. 2 depicts a flowchart of operations for quantifying drill bit wear.
Figure 3:
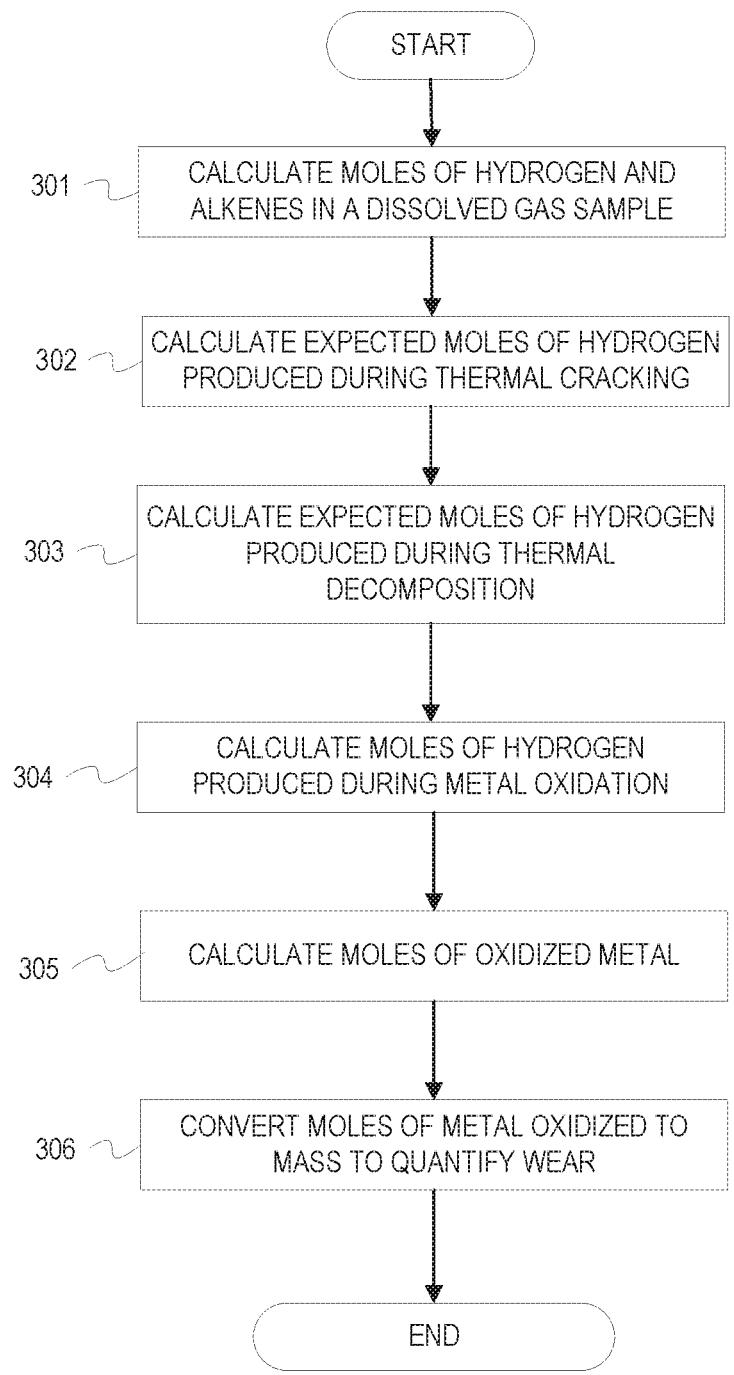
FIG. 3 depicts a flowchart of operations for calculating a mass of metal oxidized from the drill bit during drilling.

FIG. 2 and FIG. 3 depict flowcharts of example operations for quantifying drill bit wear and determining mass of oxidized metal. FIGS. 2-3 include operations that can be performed by hardware, software, firmware, or a combination thereof. For example, at least some of the operations can be performed by a processor executing program code or instructions. The description refers to the program code that performs some of the operations as a "wear evaluator," although it is appreciated that program code naming and organization can be arbitrary, language dependent, and/or platform dependent. Operations of the flowchart of FIG. 2 start at block 201.

At block 201, extractors remove dissolved gas from respective fluid flows. An extractor is connected to a fluid flow into a wellbore (flow in). Another extractor is connected to a fluid flow out of the wellbore (flow out). A conduit connects the extractors to the fluid flows. The conduit allows a transfer of liquid. The extractors remove dissolved gas from the fluid flows continuously.

At block 202, detectors detect alkenes and hydrogen in respective gas sample streams. A sample conditioning system couples each extractor to a detector or multiple detectors. The sample conditioning system cleans the dissolved gas sample with water to remove any particulates in the sample to prevent the particulates from hitting the detectors. The detectors can be a mass spectrometer and/or a gas chronograph and can be continuous or cycle based. Dissolved gas samples flow through the detectors. The detectors detect at least ethylene, propylene, and hydrogen in a gas sample stream but are also capable of detecting other gases such as carbon dioxide and oxygen. Each detector measures the molar composition of the corresponding dissolved gas sample.

At block 203, a drilling component wear evaluator ("wear evaluator") calculates the molarity of each species in each gas sample stream. Using the determined molar composition of the dissolved gas sample, the moles of each chemical species present in the dissolved gas sample can be calculated. The chemical species include at least ethylene, propylene, and hydrogen. Applying the principles of the Law of Conservation of Mass allows for the calculation of hydrogen, ethylene, and propylene present at the extractors. From the molar composition, the moles of hydrogen, ethylene, and propylene are calculated at the extractor through mass balance. The moles of each chemical species are divided by the volumetric flow of fluid through the extractor to determine the molarity of each chemical species.

At block 204, the wear evaluator quantifies the bit wear in terms of mass loss with the molarity of alkenes and hydrogen. The wear evaluator determines the moles of hydrogen and moles of alkenes in the dissolved gas sample. The wear evaluator includes a set of chemical reactions that occur during thermal cracking, thermal decomposition, and metal oxidation. The wear evaluator analyzes the set of chemical reactions and uses the determined moles of hydrogen and moles of alkenes to calculate a mass of metal oxidized from the drill bit. Further details of the analysis are described in FIG. 3.

At block 205, the wear evaluator indicates the quantified drill bit wear. This quantified drill bit wear can be used to inform a remedial action. For example, a drilling operation decision can be made. Depending on the output value and known characteristics of the drill bit, drilling may continue, or remedial action may be performed. For example, drilling parameters may be adjusted to optimize drilling conditions when drill bit wear is indicated but drill bit wear is not at a critical level that could compromise drilling. If the drill bit wear is at a critical level, indicating significant wear has occurred to compromise the structural integrity of the drill bit, a decision to remove and replace the drill bit may be made. As another example, scheduling of a remedial action can be done based on the quantified drill bit wear.

FIG. 3 depicts a flowchart of example operations for calculating a mass of metal oxidized from the drill bit during drilling. The description refers to the wear evaluator as performing the example operations.

At block 301, the wear evaluator calculates molarity of each dissolved gas chemical species produced during drill bit wear. To calculate the individual molarities produced during drill bit wear for each chemical species, the wear evaluator calculates a difference between the flow in molarities for each chemical species and the flow out molarities for each chemical species. A correction (delta) is applied through an addition of a lag calculation to the molarities to account for flow time through the wellbore. For each chemical species, the delta for each species per unit volume is multiplied by the total volumetric flow rate through the wellbore. The subtraction of the molarities for the flow in from the molarities for the flow out with the applied correction gives the total moles for each chemical species produced during drill bit wear.

At block 302, the wear evaluator determines an expected value for moles of hydrogen produced during thermal cracking. The wear evaluator sums the moles of ethylene and propylene, determined in block 301, to obtain total moles of alkenes. This is used to predict hydrogen produced based on a thermal cracking reaction. Reaction 1 is a thermal cracking reaction where the alkane is a known drilling fluid property and x is a coefficient having a unit of moles.

(1)

Reaction 1 is the thermal cracking reaction of an alkane into an alkene and hydrogen. Alkane molecules are composed of carbon atoms and hydrogen atoms. Under high temperatures, some of the atomic bonds break, resulting in smaller alkenes. The broken bonds result in free hydrogen atoms, which bond with each other to form hydrogen molecules. Reaction 1 applies to the thermal cracking process of propane ($C_3H_8$) into propylene ($C_3H_6$) and ethane ($C_2H_6$) into ethylene ($C_2H_4$). Knowing alkanes and alkenes in Reaction 1, the reaction is balanced to determine the number of moles of hydrogen produced by thermal cracking.

At block 303, the wear evaluator calculates an expected value for moles of hydrogen produced during thermal decomposition. The hydrogen produced during thermal decomposition is determined based on Reaction 2, where $C_yH_z$ is a generic chemical formula representing an alkane and y and z are coefficients and corresponding subscripts representing a number of moles or atoms, respectively.

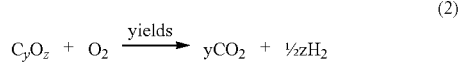
(2)

The alkane is known from the drilling fluid properties. The moles of $CO_2$ and $O_2$ can be calculated from the molar composition determined by the detectors. Reaction 2 is a chemical reaction equation representing the thermal decomposition of an alkane that occurs during bit wear. During thermal decomposition, when an alkane reacts with a diatomic oxygen molecule, the products are a metallic oxide and diatomic hydrogen molecules. Balancing Reaction 2 gives the moles of hydrogen produced during thermal decomposition. The wear evaluator then calculates an expected value for moles of hydrogen produced during thermal cracking and thermal decomposition together by summing the moles of hydrogen determined from the balancing of Reaction 1 and Reaction 2.

At block 304, the wear evaluator calculates moles of hydrogen produced during metal oxidation. Moles of hydrogen produced during thermal cracking and thermal decomposition, as determined by Reaction 1 and Reaction 2, are subtracted from the total moles of hydrogen determined at block 301.

At block 305, the wear evaluator calculates the moles of metal oxidized. Hydrogen remaining after the subtraction in block 304 are presumed to have been produced during a metal-water reaction, represented by Reaction 3, where i and j are coefficients and corresponding subscripts with units of moles or atoms, respectively.

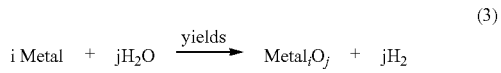
(3)

When metal reacts with water, as in Reaction 3, the metal oxidizes to produce a metal oxide and hydrogen. Knowing the products in Reaction 3 allows the moles of metal to be calculated. Gross metal composition and possible and/or average oxidation state of the metal are used in conjunction with the remaining moles of hydrogen to back-calculate the moles of metal that have been oxidized. The gross metal-composition and possible and/or average oxidation state of the metal are known properties related to the drill bit that can be looked up or predefined as a constant or statically assigned variable in the program code of the wear evaluator. Moles of metal, coefficient i in Reaction 3, is determined through stoichiometry.

At block 306, the wear evaluator converts the moles of oxidized metal to mass. The wear life evaluator converts moles of metal determined using Reaction 3 to mass using the molecular weight. The calculated mass of the metal oxidized quantifies the amount of drill bit wear that has occurred during the drilling process. The wear evaluator can use the calculated mass of oxidized metal itself as a quantification of the wear or translate/convert the calculated mass into another value that represents evaluated wear. As an example, the wear evaluator can convert the calculated mass of oxidized metal into a percentage of the drill bit. The wear evaluator can provide the quantification of drill bit wear differently. The value can be communicated or presented via a user interface or messaging (e.g., graphical user interface or text message notification).

The described reaction products presume a drill bit in an open wellbore. If the drill bit is in a casing, the reaction products are from the drill bit, collars, or drill pipe interaction with the casing. In this instance, the wear value would be a system wear value representing total wear of all the components of the system. The reactions are equilibrium controlled and only proceed from reactants to products. Accordingly, once thermal cracking, decomposition, or metal oxidation has occurred, no further reaction occurs to convert the product back to the starting reactant. This allows the Law of Conservation of Mass to be used in balancing the reactions. No chemical segregation and/or fractionation occurs in a wellbore or any other location before the detectors.

The use of both a flow in and a flow out improves the accuracy of the bit wear quantification. Alkenes do not naturally occur in a drilling fluid prior to thermal cracking or thermal decomposition reactions. However, it is possible for alkenes to be produced due to reactions that occur in other locations along the wellbore before the drilling fluid reaches the drill bit. As such, the process can be performed using only a fluid flow out. In this instance, no hydrogen, ethylene or propylene is recycled. All alkenes and hydrogen are assumed to be produced due to drill bit wear.

Figure 4:
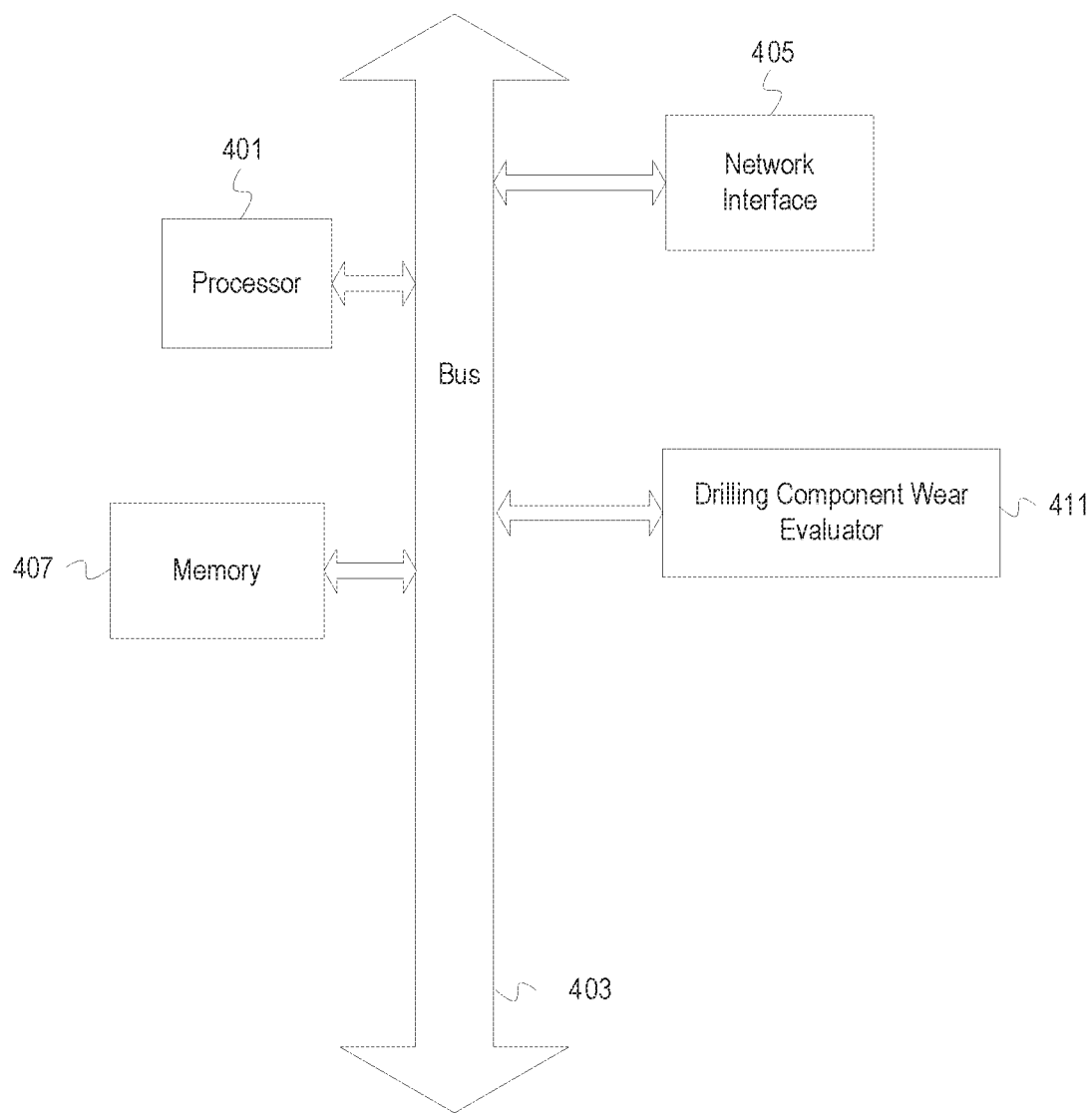
FIG. 4 depicts an example computer, according to some embodiments.

FIG. 4 depicts an example system that determines drill bit wear. The system includes a processor 401 (possibly including multiple processors, multiple cores, multiple nodes, and/or implementing multi-threading, etc.). The system includes memory 407. The memory 407 may be system memory or any one or more of the above already described possible realizations of machine-readable media. The system also includes a bus 403 and a network interface 405.

The system also includes drilling component wear evaluator 411. The drilling component wear evaluator can perform operations of predicting hydrogen production, determining gross metal composition and average oxidation state, and using molecular weight to determine mass. Any one of the previously described functionalities may be partially (or entirely) implemented in hardware and/or on the processor 401. For example, the functionality may be implemented with an application specific integrated circuit, in logic implemented in the processor 401, in a co-processor on a peripheral device or card, etc. Further, realizations may include fewer or additional components not illustrated in FIG. 4 (e.g., video cards, audio cards, additional network interfaces, peripheral devices, etc.). The processor 401 and the network interface 405 are coupled to the bus 403. Although illustrated as being coupled to the bus 403, the memory 407 may be coupled to the processor 401.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine readable storage medium may be any tangible medium that can contain, or store a program for use by or in connection with an instruction execution system, apparatus, or device. A machine readable storage medium is not a machine readable signal medium.

A machine readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine readable signal medium may be any machine readable medium that is not a machine readable storage medium and that can communicate, propagate, or transport a program for use by or in connection with an instruction execution system, apparatus, or device.

Program code embodied on a machine readable medium may be transmitted using any appropriate medium, including but not limited to wireless, wireline, optical fiber cable, RF, etc., or any suitable combination of the foregoing.

The program code/instructions may also be stored in a machine readable medium that can direct a machine to function in a particular manner, such that the instructions stored in the machine readable medium produce an article of manufacture including instructions which implement the function/act specified in the flowchart and/or block diagram block or blocks.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

As used herein, the term "or" is inclusive unless otherwise explicitly noted. Thus, the phrase "at least one of A, B, or C" is satisfied by any element from the set {A, B, C} or any combination thereof, including multiples of any element.

Example Embodiments

A method comprises calculating moles of hydrogen and moles of alkenes in a first dissolved gas sample using molar composition of the first dissolved gas sample that was extracted from a first fluid flow of a drilling fluid. Expected moles of hydrogen produced during thermal cracking and thermal decomposition are calculated based, at least in part, on the moles of alkenes in the first dissolved gas sample and moles of alkane for the drilling fluid. Moles of hydrogen produced by metal oxidation are calculated based, at least in part, on the moles of hydrogen in the first dissolved gas sample and the expected moles of hydrogen produced during thermal cracking and thermal decomposition. Moles of oxidized metal are calculated based on gross metal composition of a drill bit and the moles of hydrogen produced by metal oxidation. The moles of oxidized metal are converted to mass of metal oxidized from the drill bit. A quantification of wear of the drill bit is indicated based, at least in part, on the mass of oxidized metal.

The method further comprises calculating moles of hydrogen and moles of alkenes in a second dissolved gas sample using molar composition of the second dissolved gas sample extracted from a second fluid flow of the drilling fluid. The moles of hydrogen and moles of alkenes in the second dissolved gas are subtracted from the moles of hydrogen and moles of alkenes in the first dissolved gas sample to obtain total moles of hydrogen produced and total moles of alkenes produced. Expected moles of hydrogen produced during thermal cracking and thermal decomposition are calculated based, at least in part, on the total moles of hydrogen produced and the total moles of alkenes. The first fluid flow is flow out and the second fluid flow is flow in. A remedial action is performed based on the indicated quantification of wear of the drill bit. Calculating the moles of alkenes in the first dissolved gas sample comprises determining moles of ethylene and moles of propylene from the molar composition. Calculating the moles of alkenes in the first dissolved gas sample comprises summing the moles of ethylene and the moles of propylene. Calculating the expected moles of hydrogen produced during thermal cracking comprises mass balancing a thermal cracking chemical reaction defined by

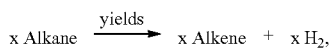

where x is a coefficient having a unit of moles. Calculating the expected moles of hydrogen produced during thermal decomposition comprises mass balancing a thermal decomposition reaction defined by

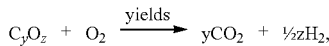

where y and z are coefficients and corresponding subscripts having units of moles or atoms, respectively. Calculating the moles of hydrogen produced by metal oxidation comprises subtracting the expected moles of hydrogen produced during thermal cracking and thermal decomposition from the moles of hydrogen in the dissolved gas. Calculating moles of oxidized metal comprises mass balancing a metal-water reaction defined by

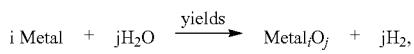

where i and j are coefficients and corresponding subscripts having units of moles or atoms, respectively.

A method comprises extracting a first dissolved gas sample from a first drilling fluid sample corresponding to a drill bit. Molar composition of hydrogen and alkenes in the first dissolved gas sample is determined. Molarity of the hydrogen and alkenes are calculated based, at least in part, on the molar composition and a volumetric flow rate corresponding to the drilling fluid sample. Expected molarity of hydrogen is calculated based on the volumetric flow rate and drilling fluid properties. Drill bit wear is quantified based on an analysis of thermal cracking, thermal decomposition, and metal-water reactions using the calculated molarities of hydrogen and alkenes present in the dissolved gas samples and the calculated expected molarity of hydrogen.

The method further comprises extracting a second dissolved gas sample from a second drilling fluid sample corresponding to the drill bit, determining molar composition of hydrogen and alkenes in the second dissolved gas sample, and calculating molarity of the hydrogen and alkenes in the second dissolved gas sample based, at least in part, on the molar composition and a volumetric flow rate corresponding to the second drilling fluid sample. The molarity of the hydrogen and alkenes in the second dissolved gas sample is subtracted from the molarity of the hydrogen and alkenes in the first dissolved gas sample to obtain total molarity of hydrogen produced and total molarity of alkenes produced. An expected molarity of hydrogen produced during thermal cracking and thermal decomposition is calculated based, at least in part, on the total molarity of hydrogen produced and the total molarity of alkenes produced.

The first drilling fluid sample corresponds to a drilling fluid flow out and the second drilling fluid sample corresponds to a drilling fluid flow in. A remedial action is performed based on the quantified drill bit wear.

Calculating the molarity of alkenes in the first dissolved gas sample comprises determining a molarity of ethylene and a molarity of propylene from the molar composition and the volumetric flow rate corresponding to the first drilling fluid sample. Calculating the molarity of alkenes in the first dissolved gas sample comprises summing the molarity of ethylene and the molarity of propylene.

A non-transitory, computer-readable medium has instructions stored thereon that are executable by a computing device to perform operations comprising calculating moles of hydrogen and moles of alkenes in a first dissolved gas sample using molar composition of the first dissolved gas sample that was extracted from a first fluid flow of a drilling fluid, calculating expected moles of hydrogen produced during thermal cracking and thermal decomposition based, at least in part, on the moles of alkenes in the first dissolved gas sample and moles of alkane for the drilling fluid, calculating moles of hydrogen produced by metal oxidation based, at least in part, on the moles of hydrogen in the first dissolved gas sample and the expected moles of hydrogen produced during thermal cracking and thermal decomposition, calculating moles of oxidized metal based on gross metal composition of a drill bit and the moles of hydrogen produced by metal oxidation, converting the moles of oxidized metal to mass of metal oxidized from the drill bit, and indicating a quantification of wear of the drill bit based, at least in part, on the mass of oxidized metal.

The non-transitory, computer-readable medium further comprises instructions executable by the computing device to perform operations comprising calculating moles of hydrogen and moles of alkenes in a second dissolved gas sample using molar composition of the second dissolved gas sample extracted from a second fluid flow of the drilling fluid, subtracting the moles of hydrogen and moles of alkenes in the second dissolved gas from the moles of hydrogen and moles of alkenes in the first dissolved gas sample to obtain total moles of hydrogen produced and total moles of alkenes produced, and calculating expected moles of hydrogen produced during thermal cracking and thermal decomposition based, at least in part, on the total moles of hydrogen produced and the total moles of alkenes.

The instructions for calculating the moles of alkenes in the first dissolved gas sample comprise instructions executable by the computing device to determine moles of ethylene and moles of propylene from the molar composition. The instructions for calculating the moles of hydrogen produced by metal oxidation comprise instructions executable by the computing device to subtract the expected moles of hydrogen produced during thermal cracking and thermal decomposition from the moles of hydrogen in the dissolved gas.

What is claimed is:

1. A method comprising:
   calculating moles of hydrogen and moles of alkenes in a
      first dissolved gas sample using molar composition of the first dissolved gas sample that was extracted from a first fluid flow of a drilling fluid;

calculating expected moles of hydrogen produced during thermal cracking and thermal decomposition based, at least in part, on the moles of alkenes in the first dissolved gas sample and moles of alkane for the drilling fluid;

calculating moles of hydrogen produced by metal oxidation based, at least in part, on the moles of hydrogen in the first dissolved gas sample and the expected moles of hydrogen produced during thermal cracking and thermal decomposition;

calculating moles of oxidized metal based on gross metal composition of a drill bit and the moles of hydrogen produced by metal oxidation;

converting the moles of oxidized metal to mass of metal oxidized from the drill bit; and indicating a quantification of wear of the drill bit based, at least in part, on the mass of oxidized metal.

2. The method of claim 1 further comprising:

calculating moles of hydrogen and moles of alkenes in a second dissolved gas sample using molar composition of the second dissolved gas sample extracted from a second fluid flow of the drilling fluid;

subtracting the moles of hydrogen and moles of alkenes in the second dissolved gas from the moles of hydrogen and moles of alkenes in the first dissolved gas sample to obtain total moles of hydrogen produced and total moles of alkenes produced; and calculating expected moles of hydrogen produced during thermal cracking and thermal decomposition based, at least in part, on the total moles of hydrogen produced and the total moles of alkenes.

3. The method of claim 2, wherein the first fluid flow is flow out and the second fluid flow is flow in.

4. The method of claim 1, further comprising performing a remedial action based on the indicated quantification of wear of the drill bit.

5. The method of claim 1, wherein calculating the moles of alkenes in the first dissolved gas sample comprises determining moles of ethylene and moles of propylene from the molar composition.

6. The method of claim 5, wherein calculating the moles of alkenes in the first dissolved gas sample comprises summing the moles of ethylene and the moles of propylene.

7. The method of claim 1, wherein calculating the expected moles of hydrogen produced during thermal cracking comprises mass balancing a thermal cracking chemical reaction defined by

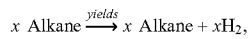
$$x\ \text{Alkane} \xrightarrow{yields} x\ \text{Alkane} + x\text{H}_2,$$

wherein x is a coefficient having a unit of moles.

8. The method of claim 1, wherein calculating the expected moles of hydrogen produced during thermal decomposition comprises mass balancing a thermal decomposition reaction defined by

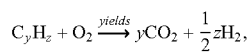
$$C_yH_z + O_2 \xrightarrow{yields} yCO_2 + \frac{1}{2}zH_2,$$

wherein y and z are coefficients and corresponding subscripts having units of moles or atoms, respectively.

9. The method of claim 1, wherein calculating the moles of hydrogen produced by metal oxidation comprises subtracting the expected moles of hydrogen produced during thermal cracking and thermal decomposition from the moles of hydrogen in the dissolved gas.

10. The method of claim 1, wherein calculating moles of oxidized metal comprises mass balancing a metal-water reaction defined by

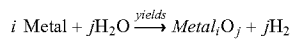
$$i\ \text{Metal} + j\text{H}_2\text{O} \xrightarrow{yields} \text{Metal}_i\text{O}_j + j\text{H}_2$$

wherein i and j are coefficients and corresponding subscripts having units of moles or atoms, respectively.

11. A non-transitory, computer-readable medium having instructions stored thereon that are executable by a computing device to perform operations comprising:

calculating moles of hydrogen and moles of alkenes in a first dissolved gas sample using molar composition of the first dissolved gas sample that was extracted from a first fluid flow of a drilling fluid;

calculating expected moles of hydrogen produced during thermal cracking and thermal decomposition based, at least in part, on the moles of alkenes in the first dissolved gas sample and moles of alkane for the drilling fluid;

calculating moles of hydrogen produced by metal oxidation based, at least in part, on the moles of hydrogen in the first dissolved gas sample and the expected moles of hydrogen produced during thermal cracking and thermal decomposition;

calculating moles of oxidized metal based on gross metal composition of a drill bit and the moles of hydrogen produced by metal oxidation;

converting the moles of oxidized metal to mass of metal oxidized from the drill bit; and indicating a quantification of wear of the drill bit based, at least in part, on the mass of oxidized metal.

12. The non-transitory, computer-readable medium of claim 11, further comprising instructions executable by the computing device to perform operations comprising:

calculating moles of hydrogen and moles of alkenes in a second dissolved gas sample using molar composition of the second dissolved gas sample extracted from a second fluid flow of the drilling fluid;

subtracting the moles of hydrogen and moles of alkenes in the second dissolved gas from the moles of hydrogen and moles of alkenes in the first dissolved gas sample to obtain total moles of hydrogen produced and total moles of alkenes produced; and calculating expected moles of hydrogen produced during thermal cracking and thermal decomposition based, at least in part, on the total moles of hydrogen produced and the total moles of alkenes.

13. The non-transitory, computer-readable medium of claim 11, wherein the instructions for calculating the moles of alkenes in the first dissolved gas sample comprise instructions executable by the computing device to determine moles of ethylene and moles of propylene from the molar composition.

14. The non-transitory, computer-readable medium of claim 11, wherein the instructions for calculating the moles of hydrogen produced by metal oxidation comprise instructions executable by the computing device to subtract the expected moles of hydrogen produced during thermal cracking and thermal decomposition from the moles of hydrogen in the dissolved gas.

\* \* \* \* \*